US008273728B2

(12) United States Patent
Thumbeck et al.

(10) Patent No.: US 8,273,728 B2
(45) Date of Patent: *Sep. 25, 2012

(54) PREFORMULATION FOR TABLETTING NATURAL MIXTURES OF CONJUGATED ESTROGENS

(75) Inventors: Bernd Thumbeck, Nordstemmen (DE); Ingo Bonnacker, Nordstemmen (DE); Martina Lerch, Langenhagen (DE)

(73) Assignee: Abbott Products GmbH, Hannover (DE)

( * ) Notice: Subject to any disclaimer, the term of this patent is extended or adjusted under 35 U.S.C. 154(b) by 1572 days.

This patent is subject to a terminal disclaimer.

(21) Appl. No.: 10/866,095

(22) Filed: Jun. 14, 2004

(65) Prior Publication Data

US 2005/0009800 A1 Jan. 13, 2005

Related U.S. Application Data

(63) Continuation of application No. PCT/EP02/14104, filed on Dec. 12, 2002.

(30) Foreign Application Priority Data

Dec. 14, 2001 (EP) .................................... 01129840

(51) Int. Cl.
*A61K 31/56* (2006.01)
(52) U.S. Cl. ........................................ 514/170; 514/182
(58) Field of Classification Search .................. 514/182, 514/170
See application file for complete search history.

(56) References Cited

U.S. PATENT DOCUMENTS

| 3,487,152 | A | 12/1969 | Carstensen et al. |
| 4,154,820 | A | 5/1979 | Simoons |
| 4,753,803 | A | 6/1988 | Klug et al. |
| 5,908,638 | A | 6/1999 | Huber et al. |

FOREIGN PATENT DOCUMENTS

| CN | 1036328 A | 10/1989 |
| CN | 1197387 A | 10/1998 |
| CN | 1298313 | 2/2007 |
| EP | 0322020 A | 6/1989 |
| JP | 62-087518 | 4/1987 |
| JP | 2000-156938 | 6/2000 |
| WO | 97 04752 A | 2/1997 |
| WO | WO 98/08525 | 3/1998 |
| WO | WO 98/08526 | 3/1998 |

OTHER PUBLICATIONS

PDF reference, 48th ed., 1994, pp. 2594-2596.*
Remington's Pharmaceutical Sciences, 18th ed., 1990, p. 1641-1647.*
Li et al., Pharmaceutical Development and Technology, 1996;1(4):343-355.*
Banks and Aultons, Drugs Development and Industrial Pharmacy, 1991;17(11):1437-1463.*
Handbook of Pharmaceutical Granulation by Parikh, Dilip M, New York Marcel Dekker, 1997.*
Worts, "Wet Granulation-Fluidized Bed and High Shear Techniques Compared," Pharmaceutical Technology Europe, 10(11): 1998, pp. 27-30.
Fiedler Encyclopedia of Excipients; $5^{th}$ ed. 2002, pp. 855-856.
Fiedler Encyclopedia of Excipients; $5^{th}$ ed. 2002, pp. 380-381.
Parmentier G: Auxiliary Agents for Direct Tabletting—A survey; In: Pharma International.
Chemistry Review of Premarin; Center for Drug Evaluation and Research.
Ritschel and Bauer-Brandl; Die Tablette—Hanbuch der Entwicklung, Herstellung und Qualitatssicherung; 2002; pp. 71-72, 95-97 and 108; 2nd Edition.
Microcrystalline Cellulose; in Pharmazeutische Pellets—Herstellung, Eigenschaften und Anwendung; Kleinbude; 2003.
Cellulose ethers; in Rompp [chemical dictionary], last update Aug. 2004.
Cellulose derivatives; in Rompp [chemical dictionary]; last update Aug. 2005.
Microcrystalline Celluclose; in Rompp Lexikon der Chemie; Aktualisierung Aug. 2005, Dokumentkennung RD-13-02326.
Kamel at al., Pharmaceutical significance of cellulose: a review; Polymer Letters; 2008; pp. 758-778; vol. 2, No. 11.
Nyqvist et al.; Studies on the physical properties of tablets and table excipients: I, Adsorption of drugs to cellulose used in tablets; in Acta Pharm.
Siepmann et al.: Modeling of drug release from delivery systems based on hydroxypropyl methylcellulose (HPC); in Advance Drug Delivery.
Trocknungsverlust, in Rompp Online, Version 3.4 [Jul. 21, 2009].
Loss of Drying; in United States Pharmacopoeia; Chapter 731 [Jan. 20, 2009].
USP Congugated estrogens.

* cited by examiner

*Primary Examiner* — San-Ming Hui
(74) *Attorney, Agent, or Firm* — Crowell & Moring LLP

(57) ABSTRACT

A pharmaceutical preformulation in the form of a solid, free-flowing dry extract of a natural mixture of conjugated equine estrogens, which is particularly suitable use in for solid galenic forms, e.g. tabletting. The conjugated estrogens are available for further galenic processing in a form which assures the chemical stability of the hormones and permits advantageous processing into solid galenic forms, for example a tablet. The invention furthermore relates to a method for producing these preformulations in the form of a dry extract.

18 Claims, No Drawings

PREFORMULATION FOR TABLETTING NATURAL MIXTURES OF CONJUGATED ESTROGENS

CROSS REFERENCE TO RELATED APPLICATIONS

This application is a continuation of international patent application no. PCT/EP02/14104, filed Dec. 12, 2002, designating the United States of America, and published in German as WO 03/051337, the entire disclosure of which is incorporated herein by reference. Priority is claimed based on European patent application no. EP 01129840.3, filed Dec. 14, 2001.

BACKGROUND OF THE INVENTION

The present invention relates to pharmaceutical preformulations in the form of a dry extract of natural mixtures of conjugated equine estrogens, in particular of mixtures of conjugated estrogens obtained from the urine of pregnant mares. Dry extracts as preformulations of these natural mixtures of conjugated estrogens suitable for the production of solid galenic forms, e.g. for tabletting, are thereby provided. The invention furthermore relates to a method for the production of these preformulations in the form of a dry extract.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated equine estrogens such as are found in the urine of pregnant mares have proved particularly effective and readily compatible.

The dissolved solids content in the urine of pregnant mares (=pregnant mares' urine, abbreviated hereafter as "PMU") can naturally vary within wide ranges, and may generally lie in a range of 40 to 90 g dry matter per liter. In addition to urea and other usual urine contents, phenolic constituents, e.g. cresols and dihydro-3,4-bis[(3-hydroxyphenyl)methyl]-2 (3H)-furanone, known as HPMF, are contained in the solids content of the PMU. The natural mixture of estrogens contained in the PMU is largely present in conjugated form, e.g. as sulfuric acid semi-ester sodium salt (abbreviated hereafter as "sulfate salt"). The content of conjugated estrogens (abbreviated hereafter as "CE"), calculated as estrogen sulfate salt and relative to dry matter, may be between 0.3 and 1% by weight.

By separating out the undesirable accompanying substances, such as urea and in particular cresols and HPMF, usually extracts are obtained from the PMU which contain the conjugated estrogens from pregnant mares' urine (PMU) in dissolved form (solution extracts). More recent methods obtain natural mixtures of these conjugated estrogens (CE) by solid-phase extraction of the mixture of conjugated estrogens from pregnant mares' urine e.g. on RP silica gel (WO 98/08525) or on semipolar, in particular on non-ionic semipolar, polymeric adsorption resins (WO 98/08526). With these methods, the undesirable accompanying substances can be separated from the PMU effectively and efficiently and aqueous solution extracts of the CE of good quality can be obtained. The concentration of the CE in the solution extract is however subject to certain unavoidable fluctuations, since the PMU used for obtaining the CE as a natural starting material per se is subject to natural fluctuations in quality owing to its origin, storage, transport and any pre-processing etc.

In the production of pharmaceutical preparations of natural mixtures of conjugated equine estrogens from CE-containing solution extracts, a constant quality and metering strength of the preparation must be ensured. The natural fluctuations in the content of conjugated equine estrogens in the solution extracts used for the production of pharmaceutical preparations which occur as a function of the yield and quality of the starting material therefore have to be compensated for by suitable measures, in order to provide a material of constant quality and defined specification for further galenic processing.

There is therefore a need for suitable improved methods for conversion of the CE-containing aqueous solution extracts obtained by working up PMU into a solid galenic preformulation which is as protective of the product as possible, which contains the natural mixture of conjugated equine estrogens as active component in defined form and concentration and in a homogeneous distribution and then can be used as solid pharmaceutical raw material containing active substance ("dry extract") in simple manner for further galenic processing into solid forms, such as for example for tabletting or direct tabletting. The natural mixture of conjugated equine estrogens must therefore be present in a form which assures the chemical stability of the hormones, i.e. the conjugated estrogens contained in the mixtures, and which permits the processing of these hormones into a solid galenic form, e.g. a tablet.

SUMMARY OF THE INVENTION

It is thus an object of the present invention to provide a solid, free-flowing pharmaceutical raw material (dry extract) as starting material for the galenic preparation of CE-containing pharmaceuticals in solid form, for example by tabletting or direct tabletting, wherein the raw material provided as starting material for the galenic processing contains a natural mixture of conjugated equine estrogens obtained from pregnant mares' urine as active component in a defined form, homogenous distribution and a defined, standardized active-substance content on a pharmaceutical support material.

It has now surprisingly been found that aqueous solution extracts obtained by working-up PMU which contain a mixture of natural conjugated equine estrogens (CE) can be applied in simple manner as active-substance constituent on to a solid pharmaceutical support material fluidized in a fluidized bed in a homogenous distribution and with a defined, standardized concentration, with active substance-coated particles of defined form being produced and the active substance, i.e. the natural mixture of conjugated equine estrogens, being present in very stable manner bound in a solid form. This pharmaceutical preformulation can be easily processed further galenically as a high-quality solid, free-flowing powder and/or granular dry extract, in particular by tabletting or direct tabletting, to form solid pharmaceutical preparations.

The present invention therefore relates to a pharmaceutical preformulation in the form of a solid, free-flowing dry extract for tabletting, characterized by (a) a standardized active-substance content (relative to the main hormone constituents) of a mixture of natural conjugated equine estrogens defined per amount of support material, wherein (b) the active-substance content is applied by spraying from an aqueous solution on to a powdered and/or granular pharmaceutical support material from the group of microcrystalline celluloses or a mixture of microcrystalline cellulose with lactose and drying.

Conjugated equine estrogens are a mixture of various conjugated forms of estrogens which are obtained from pregnant mares' urine. The two principal main constituents are sodium estrone sulfate and sodium equilin sulfate. A third essential constituent is 17-α-dihydroequilin sulfate. In addition, sodium-17-α-estradiol sulfate and sodium-17-β-dihydroequilin sulfate are also of significance. Conjugated estrogens (CE) usually contain 52.5 to 61.5% by weight sodium estrone sulfate, 22.5 to 30.5% by weight sodium equilin sulfate, 13.5 to 19.5% by weight sodium-17-α-dihydroequilin sulfate, 2.5 to 9.5% by weight sodium-17-α-estradiol sulfate and 0.5 to 4% by weight sodium-17-β-dihydroequilin sulfate. The total proportion of sodium estrone sulfate and sodium equilin sulfate is usually in the range of 79.5 to 88% by weight. The total content of free estrogens such as estrone, equilin and 17-α-dihydroequilin is usually no more than 1.3% by weight. The above percentages relate to what is called the "labelled content", as can usually be determined and calculated in accordance with European Pharmacopoeia 2001 or analogously to USP (United States Pharmacopoeia) by means of gas-chromatographic profiles, compared with reference solutions.

The active-substance content of the hormones contained in the mixture of natural conjugated equine estrogens is usually standardized relative to the main hormone constituents, in which case as a rule it is geared to the total of the three main constituents estrone, equilin and 17-α-dihydroequilin, but occasionally also to the total of these three main constituents and additionally 17-α-estradiol and 17-β-dihydroequilin (in each case conjugated and free hormones).

In advantageous embodiments of the present invention, the pharmaceutical preformulation is distinguished in that the active-substance content calculated as dry matter (DM) of an extract containing the mixture of natural conjugated equine estrogens from pregnant mares' urine (total hormone content including the free estrogens and other solids) relative to the amount of the pharmaceutical support material in the preformulation lies in the range of 0.25 to 0.70 g DM/g support material, preferably in the range of 0.28 to 0.64 g DM/g support material.

If the active-substance content (total hormone content including the free estrogens) of the pharmaceutical preformulation is calculated as a mixture of natural equine conjugated estrogens (CE) relative to the amount of the pharmaceutical support material in the preformulation, the active-substance content lies in the range of 35 to 100 mg CE/g support material, preferably in the range of 43 to 90 mg CE/g support material.

After drying the pharmaceutical preformulation obtained by spraying the CE-active-substance content from an aqueous solution on to the powdered and/or granular pharmaceutical support material from the group of microcrystalline celluloses or on to a mixture of at least one of these microcrystalline celluloses with lactose, this may, due to the way it is produced, still contain a small amount of residual moisture. Usually the residual moisture content in this case lies within the scope of the usual maximum values for the drying processes used. Thus the residual moisture in the pharmaceutical preformulation is in particular at most about 3.0% by weight, preferably at most about 1.0% by weight, relative to the total preformulation as 100% by weight (total of the active-substance content calculated as dry matter, the pharmaceutical support material and taking into account the proportion of residual moisture).

If the active-substance content of the pharmaceutical preformulation according to the invention is calculated as total hormone content (total of all conjugated and free hormones), then the active-substance content lies in the range of about 35 to 100 mg per 1 g of the pharmaceutical support material, preferably in the range of about 43 to 90 mg per 1 g of the pharmaceutical support material.

Advantageous embodiments of the pharmaceutical preformulation according to the invention are distinguished in that the conjugated hormones (in each case as sodium salt of the sulfate ester), in particular the conjugated main hormones, are contained in the active-substance content in the following proportions: 52.5 to 61.5% estrone, 22.5 to 30.5% equilin, 13.5 to 19.5% 17-α-dihydroequilin, 2.5 to 9.5% estradiol, 0.5 to 4.0% 17-β-dihydroequilin.

Furthermore, in advantageous variants of the pharmaceutical preformulation according to the invention the total proportion of free hormones in the preformulation lies in the range of at most about 2 to 3 mg per 1 g of the pharmaceutical support material. Preferably the proportion of free hormones in the active-substance content of the preformulation relative to the total content of hormones (total of all conjugated and free hormones) is below 5% by weight. Depending on the working-up of the hormone-containing aqueous solution extract used for the production of the pharmaceutical preformulation according to the invention, the proportion of free hormones relative to the total hormone content may also be considerably lower, e.g. below 2% by weight.

It has surprisingly been demonstrated that by spraying a CE-solution extract obtained from PMU on to certain pharmaceutical support materials, such as microcrystalline celluloses or mixtures of these microcrystalline celluloses with lactose, by the fluidized-bed technique, the conjugated hormones can be homogeneously applied to these support materials and that the solid, free-flowing dry extract obtained thereby is advantageously suitable for producing solid galenic forms, such as tablets. In particular, the pharmaceutical preformulations according to the invention may be distributed and compressed homogeneously into a tablet in the form of the dry extract, preferably into a matrix tablet, it being possible to achieve desired release profiles. Surprisingly, it was also shown that by selecting the pharmaceutical support material as a function of the solubility in water of the support material or support material mixture the release rate of conjugated hormones present in compressed form in a matrix tablet can be advantageously influenced. In that case, in particular the type and composition of the pharmaceutical support material or support material mixture, e.g. the type and the properties of microcrystalline cellulose and lactose, the particle size and the porosity of the active-substance granules and the particle-size distribution advantageously influence the quality of the compressibility of the resulting pharmaceutical preformulation obtained according to the invention and as a result the release profile of the conjugated hormones from a matrix tablet produced by means of this pharmaceutical preformulation. Furthermore, in addition to the above-mentioned pharmaceutical support materials or support material mixtures selected according to the invention, small quantities of further conventional tabletting auxiliaries or stabilizers may be present in small quantities in the pharmaceutical preformulation according to the invention, which makes possible further influencing of the release profile of the hormones and their stability in the pharmaceutical preformulation or solid pharmaceutical preparations produced therefrom such as tablets, in particular matrix tablets. Such tabletting auxiliaries are e.g. fillers, disintegrating agents, decomposition promoters or accelerators, dry binding agents, drying agents or adsorbents, lubricants (e.g. sliding agents, glidants or mould lubricants). These tabletting auxiliaries which have been named by way of example, or also further auxiliaries familiar to the person skilled in the art and usually used in tablet production, may be admixed to the preformulations according to the invention at most in those quantities in which they are also intended to be present in the finished matrix tablet.

The successful usability of the preformulation according to the invention for the production of solid galenic forms of natural mixtures of conjugated equine estrogen, in particular e.g. of tablets or preferably matrix tablets, is an important partial step in the production of the actual solid galenic form for therapeutic or prophylactic administration to patients, and is based, in addition to other factors, also on the type of powdered and/or granular pharmaceutical support materials selected according to the invention, namely in particular pharmaceutical support materials from the group of microcrystalline celluloses and lactose, used optionally in a mixture with microcrystalline cellulose. If the pharmaceutical support material in the pharmaceutical preformulation according to the invention is a microcrystalline cellulose, this may be a single type of microcrystalline cellulose or alternatively a mixture of different types of microcrystalline celluloses. Another variant of the invention contains mixtures of microcrystalline cellulose with lactose which are each present in powdered and/or granular form. In the variant of the preformulations according to the invention, in which mixtures of a microcrystalline cellulose with lactose are present as support material, the mixture ratio thereof may be varied within wide ranges, however advantageously care should be taken that the amount of the microcrystalline cellulose should not be below 60% by weight, preferably not below 80% by weight, and the amount of the lactose should not be above 40% by weight, preferably not above 20% by weight. Advantageous mixture ratios of microcrystalline cellulose to lactose are yielded if the weight ratio of microcrystalline cellulose to lactose lies in the range of 8:2 to 6:4, preferably in the range of 7.5:2.5 to 6.5:3.5. In an embodiment by way of example of the preformulation according to the invention, the mixture ratio of microcrystalline cellulose to lactose is about 7:3 as a weight ratio.

Microcrystalline celluloses are commercially available as pharmaceutical base material in various forms, e.g. as Avicel® (e.g. from Lehmann & Voss & Co., Hamburg, Germany), in particular as Avicel® types PH 101, PH 102, PH 102 SCG or PH 103. The microcrystalline celluloses for pharmaceutical purposes commercially available as Avicel® usually have e.g. the following general specification: water content below 5% by weight (type PH 103: below 3% by weight); ash below 10; refractive index 1.55; pH (dispersion) 5.5 to 7.0; average grain sizes for

| Type | PH 101 | PH 102 | PH 102 SCG | PH 103 |
| --- | --- | --- | --- | --- |
|  | 50 μm | 100 μm | 130 μm | 50 μm; | and a particle size distribution of:

| Type | PH 101 | PH 102 | PH 102 SCG | PH 103 |
| --- | --- | --- | --- | --- |
| 250 μm | <1% | <8% | <8% | <1% |
| 150 μm |  |  | >23% |  |
| 75 μm | <30% | >45% | >63% | <30% |

A further commercially available microcrystalline cellulose for pharmaceutical purposes usable according to the invention is sold under the trade name Vivapur®, e.g. as type Vivapur® 101 or Vivapur® 12, (e.g. by J. Rettenmaier & Söhne GmbH+Co, Rosenberg, Germany). Vivapur® 101 usually has e.g. the following general specification: loss on drying at most 6% by weight; degree of polymerisation (identity) <350; bulk density 0.26 to 0.32 g/ml; grain size distribution: $d_{10}$: <30 μm, $d_{50}$: 40 to 70 μm, $d_{90}$: >80 μm; sieve analysis (residue on the air-jet sieve): >250 μm at most 1% by weight, >75 μm at most 30% by weight, >32 μm at least 50% by weight; pH 5.0 to 7.0; sulfate ash at most 0.05% by weight. Vivapur® 12 usually has e.g. the following general specification: loss on drying at most 6% by weight; bulk density about 0.35 g/ml; ramming volume about 1.9 ml/g; average grain size 160 μm; grain size distribution: $d_{10}$: <30 μm, $d_{50}$: 40 to 70 μm, $d_{90}$: >80 μm; sieve analysis (residue on the air-jet sieve): >400 μm at most 1% by weight, >160 μm at most 50% by weight, >50 μm at least 70% by weight.

Lactose is likewise commercially available as a pharmaceutical base material as a white, sieved, crystalline, odorless powder which is readily soluble in water and practically insoluble in ethanol, e.g. as Capsulac® (from Meggle), in particular as Capsulac® 60 or Capsulac® 200. The lactose for pharmaceutical purposes commercially available as Capsulac® 60 usually has the following specification: acid- or alkaline-reacting substances at most 0.4 ml 0.1 n sodium hydroxide solution; specific rotation 54.4° to 55.9°; water (German Pharmacopoeia) 4.5 to 5.5%; loss on drying at most 0.5% by weight; sulfate ash at most 0.1% by weight; residue on ignition at most 0.1% by weight; grain size distribution (vibratory sieving, 25 g, 10 minutes): <100 μm at most 10% by weight, <630 μm at most 97% by weight. The lactose for pharmaceutical purposes commercially available as Capsulac® 200 (type EP D 80) usually has the following specification: acid- or alkaline-reacting substances at most 0.19 ml 0.1 n sodium hydroxide solution; specific rotation 55.4°; total water 5.39% by weight; loss on drying 0.17% by weight; sulfate ash 0.04% by weight; residue on ignition 0.04% by weight; grain size distribution (air-jet sieving, 10 g, 2 minutes): <32 μm 45 to 75% by weight, <100 μm at least 90% by weight.

In advantageous embodiments, the preformulations according to the invention may be characterized by further parameters, such as the particle-size distribution, the mean or average particle size, the porosity of the particles, the mean apparent density (bulk density) and/or mean bulk volume.

Advantageous pharmaceutical preformulations according to the invention have e.g. a mean bulk volume in the range of 1.8 to 3.0 ml/g. The mean apparent density (bulk density) of the pharmaceutical preformulation according to the invention lies e.g. in the range of 0.3 to 0.6 g/ml. In one alternative, the pharmaceutical preformulation according to the invention is distinguished in that the preformulation has a particle-size distribution characterized by sieve analysis as a percentage throughput total as a function of the sieve mesh size of 100% by weight of the particles for a mesh size of 500 μm, of at least 98% by weight of the particles for a mesh size of 250 μm, of about 65 to 99.5% by weight of the particles for a mesh size of 160 μm, of about 35 to 87% by weight of the particles for a mesh size of 125 μm, and fines of less than 23% by weight for a mesh size of 63 μm, in each case relative to the overall total of the sieve fractions as 100% by weight. Alternatively, the pharmaceutical preformulation according to the invention is distinguished in that the preformulation has a particle-size distribution characterized by sieve analysis as a function of the sieve mesh size of approximately 0.15 to at most 2% by weight of the particles larger than a mesh size of 250 μm, of approximately 3 to 31% by weight of the particles larger than a mesh size of 160 µm, of approximately 8 to 36% by weight of the particles larger than a mesh size of 125 µm and fines of the particles of about 3 to at most 23% by weight for a mesh size of 63 µm, in each case relative to the overall total of the sieve fractions as 100% by weight. The mean (average) particle size of the pharmaceutical preformulation according to the invention advantageously lies in the range of 50 to 250 µm, preferably in the range of 75 to 150 µm.

The present invention furthermore also relates to a method for the production of the dry extracts of natural mixtures of conjugated equine estrogens according to the invention as described above, in particular of mixtures of conjugated estrogens obtained from pregnant mares' urine, wherein pharmaceutical preformulations of natural mixtures of conjugated estrogens are provided by these dry extracts, which preformulations are suitable for the production of solid galenic forms, e.g. for the production of tablets and in particular also if desired also for direct tabletting. The method of the invention for the production of the pharmaceutical preformulation according to the invention in the form of a solid, free-flowing dry extract of the type defined above for tabletting is distinguished in that an aqueous solution which contains a mixture of natural conjugated equine estrogens as active substance is sprayed in an amount which corresponds to the defined standardized (relative to the main hormone constituents) active-substance content desired in the pharmaceutical preformulation on to a powdered and/or granular pharmaceutical support material, fluidized in a fluidized-bed apparatus, which is selected from the group of microcrystalline celluloses or a mixture of microcrystalline cellulose with lactose, and the resulting particles containing active substance are dried.

The microcrystalline cellulose types and lactose types usable in the method have already been described further above in conjunction with the pharmaceutical preformulations according to the invention.

For the method according to the invention, a CE-containing aqueous solution extract obtained from PMU of any origin can be used in a wide range of varying CE concentration, which can be obtained by the work-up method for the PMU described further above in relation to the prior art, in particular by the method described in WO 98/08526 or similar methods using semipolar, preferably non-ionic semipolar adsorption resins. Depending on the concentration of the CE and the accompanying substances possibly remaining in these extracts, these aqueous extracts may be concentrated by further removal of solvent or be set to desired active-substance contents for use in the method of the present invention by the addition of further water or of water-miscible organic solvents such as lower aliphatic alcohols.

In one variant of the method according to the invention, the aqueous solution containing active substance which is used may thus, in addition to the water, also contain other water-miscible organic solvents, in particular one or more lower aliphatic alcohols, as additional solvent. Suitable lower aliphatic alcohols are in particular those having one to four carbon atoms, for example methanol, ethanol, isopropanol or n-butanol. Methanol, ethanol or isopropanol are preferred. The organic solvents, in particular the alcohols, may also be added to the aqueous solution in a mixture with one another as additional solvent. The amount of the water-miscible organic solvent proportion, in particular the alcohol proportion, in the aqueous solution may lie in the ranges described as suitable in WO 98/08526. Other possibly suitable water-miscible solvents such as ketones or water-soluble ethers are likewise described in WO 98/08526.

Preferably in the method according to the invention aqueous solutions containing active substance, i.e. CE extract solutions or concentrates, are used which are an aqueous solution largely freed of organic solvent and suitable for galenic further processing, i.e. an essentially aqueous solution, of the CE or a concentrate of the CE largely freed of organic solvent. Purely aqueous solutions or concentrates of the natural mixture of conjugated estrogens are very much preferred in this case.

Advantageous variant embodiments of the present method according to the invention are distinguished in that the aqueous solution used has an active-substance content calculated as dry matter of the mixture of natural equine conjugated estrogens (total hormone content including the free estrogens and other solids) in the range of approximately 3.5 to 20% by weight relative to the aqueous solution as 100% by weight. Preferably the active-substance content in the aqueous solution calculated as dry matter of the natural mixture of conjugated equine estrogens lies in the range from approximately 3.5 to 14.5% by weight, relative to the aqueous solution as 100% by weight. If the active-substance content of the aqueous solution used according to the invention in the method is calculated as total hormone content (including the free estrogens), the aqueous solution used has an active-substance content in the range of 10 to 100 mg per 1 g of the aqueous solution, preferably in the range of 10 to 40 mg per 1 g of the aqueous solution.

If in the method according to the invention a concentrate is used as aqueous solution, this will advantageously have an active-substance content calculated as dry matter of the mixture of natural conjugated equine estrogens (total hormone content including the free estrogens and other solids) in the range of more than 20% by weight, relative to the concentrate as 100% by weight. If the active-substance content of the aqueous concentrate used according to the invention in the method is calculated as total hormone content (including the free estrogens) of the mixture of natural equine conjugated estrogens (CE), the concentrate used advantageously has an active-substance content of greater than 40 mg per 1 g of the concentrate (100% by weight).

Advantageously, aqueous solutions in which the total hormone content (including the free estrogens) relative to the dry matter contained in the aqueous solution as 100% by weight lies in the range of 18 to 31% by weight are used in the method according to the invention.

The method according to the invention for the production of the dry extracts or preformulations of natural mixtures of conjugated estrogens according to the invention, in particular of mixtures of conjugated estrogens obtained from pregnant mares' urine, can be carried out in any conventional fluidized-bed drying apparatus, in particular those for use in the pharmaceutical industry. Suitable fluidized-bed apparatus are e.g. the fluidized-bed apparatus "Strea I". In the method according to the invention, the powdered or granular pharmaceutical support material, e.g. the microcrystalline cellulose or a mixture of microcrystalline cellulose with lactose, is placed in the fluidized-bed apparatus in a pre-calculated production amount and fluidized by means of an air current. Then an aqueous solution containing a natural mixture of conjugated estrogens as active substance in an amount which corresponds to the active-substance content desired in the preformulation is sprayed on to the support material and the resulting particles containing active substance are dried.

The method in this case may be performed both continuously and discontinuously in batch operation and in addition to the type and amount of the support material used or in addition to the type, amount and the active-substance content of the aqueous solution used, may furthermore be controlled via method parameters familiar to the person skilled in the art in the field of fluidized beds, such as incoming and outgoing air temperatures, quantity of the air current supplied and removed, the spraying rate of the aqueous solution and also, in the case of a continuous procedure, by the rate of the introduction of solids and discharge of product and/or the dwell time of the product in the fluidized-bed apparatus.

In one advantageous variant of the method according to the invention, e.g. the temperature, regulated using the exhaust air temperature, of the preformulation product fluidized in the fluidized-bed apparatus lies in the range of 25 to 60° C., preferably in the range of 45 to 55° C. In an example of embodiment of the method according to the invention, the temperature, regulated using the exhaust air temperature, of the preformulation product fluidized in the fluidized-bed apparatus is approximately 45 to 55° C.

In another advantageous variant of the method according to the invention, e.g. the process moisture regulated via the relative humidity of the exhaust air in the fluidized-bed apparatus lies in the range of 50 to 80% r.h. (r.h.=relative humidity).

In yet another advantageous variant of the method according to the invention, e.g. the aqueous solution containing active substance which is used is sprayed at a spraying rate of 20 to 50 g/min on to the powdered and/or granular pharmaceutical support material fluidized in the fluidized-bed apparatus.

In the method according to the invention for producing the dry extracts or preformulations of natural mixtures of conjugated estrogens according to the invention, in particular of mixtures of conjugated estrogens obtained from pregnant mares' urine, in advantageous variant embodiments powdered and/or granular support materials are used which are characterized by certain particle properties and thus can be used for the deliberate control of the particle properties of the dry-extract or preformulation product. Suitable parameters for the particle properties of the powdered or granular support materials used, just like for the characterisation of the dry-extract or preformulation products produced on this basis are e.g. the particle-size distribution, the mean or average particle size, the porosity of the particles or the mean apparent density and also further parameters deemed advantageous by the person skilled in the art in the specific case. A few advantageous ranges of these particle parameters will be given below for orientation purposes.

In an advantageous variant of the method according to the invention, a powdered and/or granular pharmaceutical support material, in particular a microcrystalline cellulose, is used which has a particle-size distribution characterized by sieve analysis as a percentage throughput total as a function of the sieve mesh size of 100% by weight of the particles for a mesh size of 500 µm, of at least 99% by weight of the particles for a mesh size of 250 µm, of about 85 to 95% by weight of the particles for a mesh size of 160 µm, of about 70 to 80% by weight of the particles for a mesh size of 125 µm, and fines of up to about 50% by weight for a mesh size of 63 µm, in each case relative to the overall total of the sieve fractions as 100% by weight. Particularly advantageous powdered and/or granular pharmaceutical support materials used in the method according to the invention, in particular the microcrystalline cellulose, in this case have a mean (average) particle size in the range of 50 to 130 µm. The powdered and/or granular pharmaceutical support material used in the method according to the invention, in particular the microcrystalline cellulose, has e.g. an apparent density (bulk density) in the range of approximately 25 to 35 g/ml. Furthermore, the powdered and/or granular pharmaceutical support materials used in the method according to the invention, in particular the microcrystalline cellulose, are characterized in that the water content (loss on drying) is at most about 6% by weight.

According to the method of the invention, advantageously a starting material serving for the production of pharmaceuticals which contain the natural mixture of conjugated estrogens from PMU as active component is provided, which is advantageously suited as dry extract or preformulation of excellent quality for further processing by direct tabletting.

The method according to the invention and the preformulation according to the invention have a number of advantages in particular also compared with other procedures. CE-containing aqueous extracts with low hormone concentration can be processed. In contrast to what is observed with conventional spray-drying of such CE-containing extracts, in the method according to the invention in a fluidized bed undesirable attachments, e.g. to the nozzles, are not observed. The thermal loading of the valuable hormone constituents of the aqueous extracts used is very low in the fluidized bed in the method according to the invention. Sticky properties, e.g. agglomeration, of the CE-containing aqueous extract make themselves felt less than with other drying methods such as single-pot technology. Compared with operating methods in vacuum dryers etc., the method according to the invention is a continuously performable method which in addition—both with continuous and with discontinuous operation—permits the application of large quantities of liquid, even without over-wetting. In the method according to the invention, a broad range of extracts both with regard to the hormone concentration and to the concentration of accompanying substances can be processed. Because of this, the method is able to solve very well the problems which have to be overcome due to the natural fluctuations of the PMU-starting material in full-scale practice. It was demonstrated that the conjugated hormones can be applied homogeneously to the support materials by spraying a hormone concentrate using fluidized-bed technology on to support materials used according to the invention, such as microcrystalline cellulose or optionally mixtures of microcrystalline cellulose with lactose. The preformulations produced in accordance with the method according to the invention in the form of solid, free-flowing dry extracts are very stable powdered or particulate hormone-containing products, which can be homogeneously distributed in matrix tablets and compressed surprisingly well. Thus matrix tablets with a desired release profile can be produced from the pharmaceutical preformulations according to the invention in simple manner.

The following examples are intended to illustrate the invention in further detail without limiting its scope.

EXAMPLES

Example 1

Drying and Production of a Preformulation with Hormone-Containing Active Substance in a Fluidized-Bed Apparatus, and Hormone Content A series of tests were carried out with the aim of developing a hormone-containing active substance by drying the hormones from urine concentrate from pregnant mares. The conjugated hormones in this case had to be put into a form which guarantees the chemical stability of the hormones and permits processing of the hormones into a tablet. A urine concentrate (concentrated aqueous solution of pregnant mares' urine=PMU) from a collecting campaign in Asia was used, which was characterized by its amount of dry matter and hormone concentration. The urine concentrate was worked up before use in accordance with the method of WO 98/08526, in order to separate off undesirable accompanying substances such as urea, HPMF and cresols.

In the tests, it was demonstrated that the conjugated hormones could be applied homogeneously to the auxiliaries by spraying the hormone concentrate on to support materials such as microcrystalline cellulose or mixtures of microcrystalline cellulose with lactose using fluidized-bed technology.

A urine concentrate provided from a collecting campaign was sprayed on to microcrystalline cellulose or on to a mixture of microcrystalline cellulose and lactose and the hormones were thereby applied to the support or the mixture of support materials. This process was carried out in a fluidized-bed granulator. The particle size and porosity of the active-substance granules were regulated by the incoming and exhaust air temperatures and the spraying rate. The product temperature (regulated using the exhaust air temperature), which was set in the range of 25 to 55° C., and the process humidity (regulated via relative exhaust air humidity), which was set in the range of 50 to 80% relative air humidity, served as parameters for the process. The spraying rate was selected accordingly in order to maintain the aforementioned ranges.

In these tests, a fluidized-bed apparatus (Strea 1) was used for the production of dry extracts of natural mixtures of conjugated estrogens, with which about 1 kg dry extract per batch can be produced. The aqueous solution extract containing a natural mixture of conjugated estrogens was introduced into the fluidized-bed apparatus using the top-spray method. The further industrial equipment comprised:

Sartorius balance/6.2 kg/type LC6200S-OD2, tubing pump Masterflex 07523-27 with pump head 7518-10, moisture measuring apparatus of the type HR 73 from Mettler Toledo.

The tests in the fluidized-bed apparatus were carried out with aqueous solution extracts containing a natural mixture of conjugated estrogens which came from a collecting campaign in Asia which was worked up in accordance with the method described in WO 98/08526, the hormone-containing aqueous extracts having the following hormone contents:

Test 1: DM=9.2% by weight

Test 2: DM=15.9% by weight

Test 3: DM=19.3% by weight

Test 4: DM=9.2% by weight

In further tests, CE-containing aqueous solution extracts with DM=11.8% by weight (Test 5) or DM=9.9% by weight (Test 6) were used. The aqueous solution extracts all had a crystalline or oily deposit, which impaired homogeneous processing, but not substantially. The aqueous solution extracts had only a relatively low hormone content, which is why the dry extracts were set to a theoretical desired content of 45 mg conjugated estrogens per g dry extract.

There were used as support materials for the natural mixture of conjugated estrogens:

Avicel PH 102,

Capsulac 60.

Performance of the Tests

Production of a dry extract with a content of 45 mg conjugated estrogens per g dry extract for receiving solutions of 570 to 680 g of the support material.

| Test 1: | |
|---|---|
| Extract used: | 4023.1 g; DM = 9.2% by weight; Density: 1.0365 g/l; CE = 12.14 g/l |
| Receiving solution: | 677.0 g Avicel PH 102 |
| Spraying rate: | 40-50 g/min (approximate mean value) |
| Relative exhaust air humidity: | 70-80% |
| Exhaust air temperature: | 32-34° C. |

| Test 2: | |
|---|---|
| Extract used: | 2400.0 g; DM = 15.9% by weight; Density: 1.0662 g/l; CE = 20.86 g/l |
| Receiving solution: | 661.9 g Avicel PH 102 |
| Spraying rate: | 40-50 g/min (approximate mean value) |
| Relative exhaust air humidity: | 70-80% |
| Exhaust air temperature: | 32-34° C. |

| Test 3: | |
|---|---|
| Extract used: | 1904.6 g; DM = 19.3% by weight; Density: 1.0662 g/l; CE = 20.86 g/l |
| Receiving solution: | 574.8 g Avicel PH 102 |
| Spraying rate: | 40-50 g/min (approximate mean value) |
| Relative exhaust air humidity: | 70-80% |
| Exhaust air temperature: | 32-34° C. | all three tests took place without problems. The spraying times for Test 1 were 83 minutes, for Test 2 46 minutes and for Test 3 35 minutes.

| Test 4: | |
|---|---|
| Extract used: | 4023.1 g; DM = 9.2% by weight; Density: 1.0365 g/l; CE = 12.14 g/l |
| Receiving solution: | 677.0 g Avicel PH 102 |
| Spraying rate: | 40-50 g/min (approximate mean value) |
| Relative exhaust air humidity: | 50-60% |
| Exhaust air temperature: | 35-40° C. |

This test is a repetition of Test 1, which is intended to check whether a finer dry extract can be produced by reducing the spraying rate. The dry extract in sieve analyses proved to be finer than the dry extract obtained in Test 1 (see summary of the results of the tests).

Further tests were carried out using analogous procedures to Tests 1 to 3 with Avicel PH 102 (Test 5) or with mixtures of Avicel PH 102 and Capsulac 60 (weight ratio 7:3; Test 6).

Test Results

Detailed results on the hormone content in Tests 1 to 4 are compiled in Tables I to IV.

In principle it was discovered that, for a receiving solution of 570 g to 680 g Avicel PH 102 as support material, continuous and rapid application of the extract is possible (Tests 1 to 3). For the amounts of extract used, which varied from 1900 to 4023 g, the spraying times for these tests were between 35 and 83 minutes. This yielded applied amounts of 0.55 g to 0.64 g solids from the extract per g Avicel (mean value: 0.59 g).

In order in a further test (Test 5) to maintain the preset desired content of 45 mg conjugated estrogens per g dry extract or to determine limits for maximum quantities of active substance which can be applied, in this test the receiving solution of Avicel PH 102 was reduced to 342.5 g, compared with the previous Tests 1 to 4, i.e. a reduction of almost 50%. 4640 g extract was to be applied. In this case, for up to about 1600 g extract sprayed on no problems occurred, since up to this amount as in the preceding Tests 1 to 4 again there was an applied amount of 0.56 g solids from the extract per g Avicel. For about 2000 g extract sprayed on, an applied amount of 0.68 g was yielded, and for about 2500 g an amount of 0.86 g solids from the extract per g Avicel. Up to this applied amount, the extract could be sprayed on largely without problems. Thereafter, the spraying rate was greatly reduced, since from this amount onwards the solids from the extract exceed the amount of the support material and the product exhibits a tendency to stick from this point onwards. The process was then only operated at a relative humidity of <25%, since the exhaust-air filters clogged up; the amount of air was no longer sufficient to maintain the fluidized bed. The pure spraying time was more than 5 hours.

In summary, it can therefore be said that an application of up to 0.6 g solids from the extract per g Avicel the entire extract should be processed. The upper limit of quantities of extract which Avicel PH 102 can take without being impaired lies at about 0.86 g application of solids from the extract. Thereafter, it is necessary to reduce the spray application and to adapt the remaining parameters accordingly.

Test 4 is a repetition of Test 1. Here, a finer trituration was produced by changing the parameters (lower spraying rate and hence higher exhaust air temperature and lower exhaust air humidity).

In the additional Test 6, as in Test 4, a reduction in the receiving solution was effected, in order to be able to set to 45 mg conjugated estrogens per g trituration (reduction>60% compared with Test 1 and Test 2).

Additionally, lactose was used in this case (ratio of Avicel to lactose=7 to 3). In this test, from an applied quantity of 0.6 g solids from the extract per gram of Avicel/lactose mixture onwards, it was necessary to lower the spraying rate from 20 g/min to <9 g/min (at V-140 the limit was at 0.86 g solids). The amount of extract sprayed on at this moment was about 40% by weight (<1600 g). From about 1800 g onwards, here too, as already observed in Test 4, there was a tendency to stick. The test was discontinued after application of 70% amount of extract, since it was not possible to reduce the spraying rate further (<9 g/min) due to the apparatus.

TABLE I

Hormone content for Test 1

| | Total estrogens | | | | Free estrogens | | | |
|---|---|---|---|---|---|---|---|---|
| | Solution extract | | Dry extract | | Solution extract | | Dry extract | |
| Estrogens | [mg/g] | [%][1] | [mg/g] | [%][1] | [mg/g] | [%][2] | [mg/g] | [%][2] |
| 17-α-estradiol | 0.455 | 4.34 | 1.856 | 4.31 | 0.047 | | 0.196 | |
| 17-β-estradiol | 0.646 | 6.17 | 2.631 | 6.12 | 0.082 | | 0.344 | |
| 17-α-DH-equilin | 1.270 | 12.12 | 5.160 | 11.99 | 0.098 | 0.94 | 0.405 | 0.94 |
| 17-β-DH-equilin | 0.322 | 3.07 | 1.323 | 3.08 | 0.019 | | 0.077 | |
| 17-α-DH-equilenin | 0.057 | 0.54 | 0.229 | 0.53 | 0.007 | | 0.021 | |
| 17-β-DH-equilenin | 0.031 | 0.30 | 0.215 | 0.50 | 0.000 | | 0.000 | |
| Estrone | 6.193 | 59.12 | 25.371 | 58.97 | 0.247 | 2.36 | 1.015 | 2.36 |
| Equilin | 2.236 | 21.34 | 9.312 | 21.64 | 0.057 | 0.54 | 0.229 | 0.53 |
| δ-8,9-dehydroestrone | 0.293 | 2.80 | 1.223 | 2.84 | 0.022 | | 0.076 | |
| Equilenin | 0.124 | 1.18 | 0.515 | 1.20 | 0.000 | | 0.000 | |
| Total hormone content | 11.627 | | 47.835 | | 0.579 | | 2.363 | |
| Total main hormones[3] | 10.476 | | 43.022 | | 0.468 | | 1.922 | |

[1]relative to 17-α-estradiol, 17-α-DH-equilin, 17-β-DH-equilin, estrone and equilin
[2]relative to total of 17-α-estradiol, 17-α-DH-equilin, 17-β-DH-equilin, estrone and equilin from total estrogens
[3]total of the hormones 17-α-estradiol, 17-α-DH-equilin, 17-β-DH-equilin, estrone and equilin

TABLE II

Hormone balance for Test 2

| | Total estrogens | | | | Free estrogens | | | |
|---|---|---|---|---|---|---|---|---|
| | Solution extract | | Dry extract | | Solution extract | | Dry extract | |
| Estrogens | [mg/g] | [%][1] | [mg/g] | [%][1] | [mg/g] | [%][2] | [mg/g] | [%][2] |
| 17-α-estradiol | 0.826 | 4.46 | 2.085 | 4.49 | 0.087 | | 0.223 | |
| 17-β-estradiol | 1.220 | 6.58 | 3.074 | 6.62 | 0.163 | | 0.417 | |
| 17-α-DH-equilin | 2.302 | 12.42 | 5.824 | 12.54 | 0.177 | 0.96 | 0.437 | 0.94 |
| 17-β-DH-equilin | 0.634 | 3.42 | 1.506 | 3.24 | 0.036 | | 0.087 | |
| 17-α-DH-equilenin | 0.124 | 0.57 | 0.298 | 0.64 | 0.012 | | 0.030 | |
| 17-β-DH-equilenin | 0.103 | 0.56 | 0.242 | 0.52 | 0.000 | | 0.000 | |
| Estrone | 10.835 | 58.47 | 27.056 | 58.28 | 0.423 | 2.28 | 1.056 | 2.27 |
| Equilin | 3.934 | 21.23 | 9.957 | 21.45 | 0.092 | 0.50 | 0.223 | 0.50 |

TABLE II-continued

Hormone balance for Test 2

| Estrogens | Total estrogens | | | | Free estrogens | | | |
| --- | --- | --- | --- | --- | --- | --- | --- | --- |
| | Solution extract | | Dry extract | | Solution extract | | Dry extract | |
| | [mg/g] | [%][1] | [mg/g] | [%][1] | [mg/g] | [%][2] | [mg/g] | [%][2] |
| δ-8,9-dehydroestrone | 0.529 | 2.85 | 1.348 | 2.90 | 0.016 | | 0.079 | |
| Equilenin | 0.220 | 1.19 | 0.543 | 1.17 | 0.000 | | 0.000 | |
| Total hormone content | 20.727 | | 51.933 | | 1.006 | | 2.562 | |
| Total main hormones[3] | 18.531 | | 46.428 | | 0.815 | | 2.036 | |

[1]relative to 17-α-estradiol, 17-α-DH-equilin, 17-β-DH-equilin, estrone and equilin
[2]relative to total of 17-α-estradiol, 17-α-DH-equilin, 17-β-DH-equilin, estrone and equilin from total estrogens
[3]total of the hormones 17-α-estradiol, 17-α-DH-equilin, 17-β-DH-equilin, estrone and equilin

TABLE III

Hormone content for Test 3

| Estrogens | Total estrogens | | | | Free estrogens | | | |
| --- | --- | --- | --- | --- | --- | --- | --- | --- |
| | Solution extract | | Dry extract | | Solution extract | | Dry extract | |
| | [mg/g] | [%][1] | [mg/g] | [%][1] | [mg/g] | [%][2] | [mg/g] | [%][2] |
| 17-α-estradiol | 1.003 | 4.64 | 2.208 | 4.57 | 0.102 | | 0.227 | |
| 17-β-estradiol | 1.402 | 6.49 | 3.072 | 6.36 | 0.166 | | 0.365 | |
| 17-α-DH-equilin | 2.678 | 12.40 | 5.984 | 12.39 | 0.207 | 0.96 | 0.463 | 0.96 |
| 17-β-DH-equilin | 0.633 | 2.93 | 1.432 | 2.96 | 0.038 | | 0.091 | |
| 17-α-DH-equilenin | 0.118 | 0.55 | 0.232 | 0.48 | 0.021 | | 0.031 | |
| 17-β-DH-equilenin | 0.045 | 0.21 | 0.057 | 0.12 | 0.000 | | 0.000 | |
| Estrone | 12.713 | 58.87 | 28.105 | 58.18 | 0.492 | 2.28 | 1.083 | 2.24 |
| Equilin | 4.569 | 21.16 | 10.582 | 21.90 | 0.107 | 0.50 | 0.241 | 0.50 |
| δ-8,9-dehydroestrone | 0.539 | 2.50 | 1.265 | 2.62 | 0.021 | | 0.113 | |
| Equilenin | 0.222 | 1.03 | 0.492 | 1.02 | 0.000 | | 0.000 | |
| Total hormone content | 23.922 | | 53.429 | | 1.154 | | 2.614 | |
| Total main hormones[3] | 21.596 | | 48.311 | | 0.946 | | 2.105 | |

[1]relative to 17-α-estradiol, 17-α-DH-equilin, 17-β-DH-equilin, estrone and equilin
[2]relative to total of 17-α-estradiol, 17-α-DH-equilin, 17-β-DH-equilin, estrone and equilin from total estrogens
[3]total of the hormones 17-α-estradiol, 17-α-DH-equilin, 17-β-DH-equilin, estrone and equilin

TABLE IV

Hormone content for Test 4

| Estrogens | Total estrogens | | | | Free estrogens | | | |
| --- | --- | --- | --- | --- | --- | --- | --- | --- |
| | Solution extract | | Dry extract | | Solution extract | | Dry extract | |
| | [mg/g] | [%][1] | [mg/g][1] | [%] | [mg/g] | [%][2] | [mg/g] | [%][2] |
| 17-α-estradiol | 0.646 | 4.56 | 2.284 | 4.56 | 0.057 | | 0.201 | |
| 17-β-estradiol | 1.093 | 7.71 | 3.798 | 7.58 | 0.151 | | 0.531 | |
| 17-α-DH-equilin | 1.876 | 13.23 | 6.367 | 12.71 | 0.134 | 0.94 | 0.484 | 0.97 |
| 17-β-DH-equilin | 0.523 | 3.69 | 1.768 | 3.53 | 0.018 | | 0.109 | |
| 17-α-DH-equilenin | 0.070 | 0.49 | 0.274 | 0.55 | 0.008 | | 0.030 | |
| 17-β-DH-equilenin | 0.000 | 0.00 | 0.103 | 0.21 | 0.000 | | 0.000 | |
| Estrone | 8.022 | 56.57 | 28.947 | 57.77 | 0.282 | 1.99 | 1.038 | 2.07 |
| Equilin | 3.114 | 21.96 | 10.743 | 21.44 | 0.068 | 0.50 | 0.229 | 0.46 |
| δ-8,9-dehydroestrone | 0.381 | 2.69 | 1.339 | 2.67 | 0.022 | | 0.083 | |
| Equilenin | 0.119 | 0.84 | 0.543 | 1.08 | 0.000 | | 0.000 | |
| Total hormone content | 15.844 | | 56.166 | | 0.740 | | 2.705 | |
| Total main hormones[3] | 14.181 | | 50.109 | | | | 2.057 | |

[1]relative to 17-α-estradiol, 17-α-DH-equilin, 17-β-DH-equilin, estrone and equilin
[2]relative to total of 17-α-estradiol, 17-α-DH-equilin, 17-β-DH-equilin, estrone and equilin from total estrogens
[3]total of the hormones 17-α-estradiol, 17-α-DH-equilin, 17-β-DH-equilin, estrone and equilin

Evaluation of the Test Results

The production of a dry extract in the fluidized-bed apparatus, even with support materials of different grain-size distribution, is not problematic. The yield determined for all tests was between 90 and 95%. The hormone distribution, relative to 17-α-DH-equilin, estrone and equilin, is constant in the extract and in the trituration. The drying process therefore has no influence on the stability of the hormones. The residual moisture content was between 3 and 6% r.h.

As the tests show, it is possible to process large quantities of hormone-containing extract of 2 to 4 kg within a short time, i.e. to apply it to support materials and dry it accordingly. The maximum applied amounts determined (g solids from the extract per g support material, e.g. Avicel) which can be applied to the selected support material without process problems should be emphasized as being particularly important. In this case it was established that when e.g. Avicel is used as support material an application of up to about 0.6 g active-substance dry matter from the hormone-containing aqueous solution extract per g Avicel is completely without problems (Tests 1, 2 and 3 of Example 1).

Example 2

Production of Dry Extracts Using Aqueous Hormone Extract Solutions with Varying Hormone Content Further spraying tests were carried out to apply an aqueous solution extract, containing natural mixtures of equine conjugated estrogens in various concentrations, on a pharmaceutical support material selected from the group of microcrystalline celluloses. The spraying tests were carried out analogously to Example 1 in a fluidized-bed spraying apparatus with 6 different aqueous solution extracts A to F. The properties of the aqueous solution extracts A to F used (active substance solutions) and the process parameters used in each case can be seen from Table V. Further properties of the pharmaceutical preformulations obtained in the form of a solid, free-flowing dry extract are given in Table VI.

The pharmaceutical preformulations obtained in the form of a solid, free-flowing dry extract were then subjected to sieve analysis. The sieve analysis was carried out with a Retsch sieving machine under the following conditions: 5 min. sieving time, pulse time 3 s, oscillation amplitude 1.50 mm, amount of sample approx. 20 g each time. Sieves with a mesh size of from 1000 μm onwards were used. The results of the sieve analyses are reproduced in Table VII.

TABLE V

Production of dry extract fractions, containing natural mixtures of equine conjugated estrogens, tests in a fluidized-bed spray dryer

| | Active substance solutions | | | | | |
|---|---|---|---|---|---|---|
| | A DM [%] | | | B | | |
| | 3.5 CE [mg/g]: | | | 7.4 | | |
| | 10.726 CE/DM [%] | | | 17.655 | | |
| "TEF" Ch. B.: | 30.65 V-A-1 | V-A-2 | V-A-3 | V-B-1 | 23.9 V-B-2 | V-B-3 |
| Batch [g]: | 2300.00 | 2300.00 | 986.56 | 2295.08 | 2295.08 | 2295.08 |
| Conc. extract soln. [g] | 18227.0 | 18227.0 | 8278.0 | 11049.0 | 11049.0 | 11049.0 |
| Product temp. [° C.] | 45-50 | 60 | 45-50 | 45-50 | 45-50 | 45-50 |
| Incoming air temp. [° C.] | 117-121 | 114-121 | 112-120 | 91-119 | 100-119 | 118-121 |
| Exhaust air temp. [° C.] | 43-45 | 50-57 | 42-43 | 42-47 | 39-47 | 39-48 |
| Exhaust air humidity [% r.h.] | 23-36 | 14-17 | 27-31 | 21-29 | 19-29 | 22-35 |
| Spraying rate [g/min] | 34-40 | 20-30 | 21-34 | 30-39 | 30-46 | 37-43 |
| Amount of air [m³/h] | 80-100 | 80-100 | 70-85 | 80-100 | 80-100 | 80-100 |
| Spraying time [h:m] | 07:58 | 12:17 | 04:25 | 02:05 | 04:50 | 04:43 |
| with process interrupted [Y/N] | Y | Y | N | Y | N | N |
| Residual moisture [%] | 2.7 | 3.2 | 2.7 | 2.1 | 2.5 | 2.7 |
| | Active substance solutions | | | | | |
| | C DM [%] | | D | | E | F |
| | 12.7 CE [mg/g]: | | 14.5 | | 6.6 | 13.6 |
| | 33.451 CE/DM [%] | | 26.274 | | 16.229 | 38.224 |
| "TEF" Ch. B.: | 26.34 V-C-1 | V-C-2 | 18.12 V-D-1 | V-D-2 | 24.59 V-E | 28.11 V-F |
| Batch [g]: | 2295.08 | 2166.23 | 2265.40 | 2265.40 | 2321.61 | 2335.91 |
| Conc. extract soln. [g] | 5833.2 | 5504.4 | 7760.0 | 7760.0 | 12224.0 | 5500.0 |
| Product temp. [° C.] | 45-50 | 45-50 | 55 | 45-50 | 45-50 | 46-50 |

TABLE V-continued

Production of dry extract fractions, containing natural mixtures of equine conjugated estrogens, tests in a fluidized-bed spray dryer

| Incoming air temp. [° C.] | 102-121 | 106-120 | 94-117 | 86-118 | 96-120 | 87-116 |
|---|---|---|---|---|---|---|
| Exhaust air temp. [° C.] | 38-46 | 43-45 | 50-53 | 44-46 | 43-46 | 45-50 |
| Exhaust air humidity [% r.h.] | 21-36 | 25-31 | 17-19 | 19-29 | 24-32 | 28-36 |
| Spraying rate [g/min] | 36-45 | 30-42 | 40-52 | 27-37 | 32-36 | 30 |
| Amount of air [m³/h] | 80-90 | 80-95 | 110-170 | 80-130 | 80-100 | 80-100 |
| Spraying time [h:m] | 02:40 | 02:30 | 01:05 | 04:18 | 06:03 | 03:25 |
| with process interrupted [Y/N] | N | N | Y | Y | Y | N |
| Residual moisture [%] | 2.7 | 2.6 | 2.5 | 2.5 | 2.5 | 2.9 |

TABLE VI

Properties according to Example 2 of resulting pharmaceutical preformulations which contain a natural mixture of conjugated equine estrogens as solid, free-flowing dry extract fraction.

| Test No. | DM [%] CE [mg/g] CE/DM [%] | g dry matter/ 1 g support material (Vivapur 101) | mg CE content per g support material | Bulk volume [ml/g] | density [g/ml] |
|---|---|---|---|---|---|
| V-A-1 | 3.5 | 277.3 | 85 | 2.36 | 0.42 |
| V-A-2 | 10.726 | | | 2.12 | 0.47 |
| V-A-3 | 30.65 | 293.6 | 90 | 2.16 | 0.46 |
| V-B-1 | 7.4 | 355.6 | 85 | 2.48 | 0.4 |
| V-B-2 | 17.655 | | | 2.5 | 0.4 |
| V-B-3 | 23.9 | | | 2.68 | 0.37 |
| V-C-1 | 12.7 33.451 | 322.8 | 85 | 2.84 | 0.35 |
| V-C-2 | 26.34 | 322.7 | | 2.44 | 0.41 |
| V-D-1 | 14.5 26.274 | 496.7 | 90 | 2.28 | 0.44 |
| V-D-2 | 18.12 | | | 2.12 | 0.47 |
| V-E | 6.6 16.229 24.59 | 347.5 | 90 | 2.28 | 0.44 |
| V-F | 13.6 38.224 28.11 | 320.2 | 90 | 2.4 | 0.42 |

TABLE VII

Sieve analyses in accordance with Example 2 of resulting pharmaceutical preformulations in the form of solid, free-flowing dry extracts.

| Mesh size (μm) | V-A-1 V-A-2 V-A-3 TT (%) | SR (%) | V-B-1 V-B-2 V-B-3 TT (%) | SR (%) | V-C-1 V-C-2 TT (%) | SR (%) | V-E TT (%) | SR (%) | V-F TT (%) | SR (%) | Avicel PH 102 TT (%) | SR (%) | Vivapur 101 TT (%) | SR (%) |
|---|---|---|---|---|---|---|---|---|---|---|---|---|---|---|
| 1000 | 100 | 0 | 100 | 0 | 100 | 0 | 100 | 0 | 100 | 0 | 100 | 0 | 100 | 0 |
|  | 100 | 0 | 100 | 0 | 100 | 0 |  |  |  |  |  |  |  |  |
|  | 100 | 0 | 100 | 0 |  |  |  |  |  |  |  |  |  |  |
| 500 | 100 | 0 | 100 | 0 |  |  | 100 | 0 | 100 | 0 | 100 | 0 | 100 | 0 |
|  | 100 | 0 | 100 | 0 | 100 | 0 |  |  |  |  |  |  |  |  |
|  | 100 | 0 | 100 | 0 | 100 | 0 |  |  |  |  |  |  |  |  |
| 250 | 99.59 | 0.41 | 99.17 | 0.83 | 99.20 | 0.80 | 99.39 | 0.61 | 98.33 | 1.67 | 99.48 | 0.52 | 100 | 0 |
|  | 99.75 | 0.25 | 99.17 | 0.83 | 99.81 | 0.19 |  |  |  |  |  |  |  |  |
|  | 99.85 | 0.15 | 98.33 | 1.67 |  |  |  |  |  |  |  |  |  |  |
| 160 | 92.88 | 6.71 | 88.88 | 10.28 | 81.55 | 17.66 | 83.09 | 16.30 | 86.30 | 12.02 | 88.70 | 10.78 | 100 | 0 |
|  | 96.44 | 3.31 | 81.00 | 18.17 | 95.66 | 4.15 |  |  |  |  |  |  |  |  |
|  | 95.54 | 4.32 | 67.32 | 31.01 |  |  |  |  |  |  |  |  |  |  |
| 125 | 71.77 | 21.11 | 66.31 | 22.58 | 57.14 | 24.40 | 47.53 | 35.56 | 70.83 | 15.47 | 76.84 | 11.87 | 99.65 | 0.35 |
|  | 86.71 | 9.73 | 54.26 | 26.74 | 86.78 | 8.88 |  |  |  |  |  |  |  |  |
|  | 78.70 | 16.84 | 37.94 | 29.98 |  |  |  |  |  |  |  |  |  |  |
| 63 | 9.82 | 61.95 | 12.68 | 53.62 | 8.85 | 48.29 | 6.72 | 40.80 | 15.37 | 55.45 | 43.73 | 33.11 | 59.96 | 39.69 |
|  | 21.06 | 65.65 | 6.57 | 47.69 | 22.53 | 64.25 |  |  |  |  |  |  |  |  |
|  | 13.97 | 64.73 | 3.93 | 33.42 |  |  |  |  |  |  |  |  |  |  |
| Fines |  | 9.82 |  | 12.68 |  | 8.85 |  | 6.72 |  | 15.37 |  | 43.73 |  | 59.96 |
|  |  | 21.06 |  | 6.57 |  | 22.53 |  |  |  |  |  |  |  |  |
|  |  | 13.97 |  | 3.93 |  |  |  |  |  |  |  |  |  |  |

1) TT = throughput total
2) SR = sieve residue

Example 3

Orienting Tabletting Tests

In order to test the galenic further processing ability of the dry extracts or preformulations produced in Example 1 by fluidized-bed technology, the dry extracts or preformulations were mixed with further tabletting auxiliaries and compressed to form matrix tablets. It was demonstrated that the mixtures could be homogeneously distributed in a matrix tablet and compressed. Surprisingly, it was demonstrated that by selecting the support material and the further tabletting auxiliaries as a function of the solubility of the support material and tabletting-auxiliary mixture in water the release rate of the conjugated hormones compressed in the matrix tablets can be decisively influenced, and that thus desired, preset release profiles can be set. Also the composition of the support material used as support for the conjugated estrogens, e.g. of the mixture of microcrystalline cellulose with lactose, the particle size and the porosity of the active-substance granules, and also the particle-size distribution influence the quality of the compressibility and the release profile of the hormones which are released from the matrix.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pharmaceutical preformulation in the form of a tabletable, solid, free-flowing, dry extract;
   (a) wherein said solid extract contains a uniform amount of a mixture of natural conjugated equine estrogens per amount of support material, defined relative to the main hormone constituents;
   (b) wherein the uniform active-substance content is applied by spraying an aqueous solution consisting essentially of an extract of said mixture of natural conjugated equine estrogens from pregnant mares' urine onto a powdered or granular pharmaceutical support material consisting essentially of material selected from the group consisting of microcrystalline celluloses and mixtures of microcrystalline cellulose with lactose, and thereafter drying,
   (c) wherein said preformulation has the active-substance content including free estrogens and other solids calculated as dry matter relative to the amount of the pharmaceutical support material in the preformulation lying in the range from 0.25 to 0.70 gram of dry matter per gram of support material;
   (d) wherein said preformulation has the active-substance content calculated as the ratio of said mixture of natural equine conjugated estrogens relative to the amount of the pharmaceutical support material lying in the range from 35 to 100 mg of conjugated estrogens per gram of support material;
   (e) wherein said preformulation contains conjugated estrogens in the following proportions:
      52.5 to 61.5% estrone;
      22.5 to 30.5% equilin;
      13.5 to 19.5% 17-α-dihydroequilin;
      2.5 to 9.5% estradiol, and
      0.5 to 4.0% 17-β-dihydroequilin;
   (f) wherein in said preformulation the proportion of free hormones relative to the total hormone content in the active substance is less than 5% by weight; and
   (g) wherein the preformulation has a particle-size distribution corresponding to the following sieve analysis:
      100% by weight of the particles pass through a sieve mesh size of 500 µm;
      at least 98% by weight of the particles pass through a sieve mesh size of 250 µm;
      about 65 to 99.5% by weight of the particles pass through a sieve mesh size of 160 µm;
      about 35 to 87% by weight of the particles pass through a sieve mesh size of 125 µm; and
      fines of less than 23% by weight passing through a sieve mesh size of 63 µm.

2. A preformulation according to claim 1, wherein said preformulation has the active substance content lying in the range from 0.28 to 0.64 gram of dry matter per gram of support material.

3. A preformulation according to claim 1, wherein said preformulation has the active substance content calculated as the ratio of said mixture of natural equine conjugated estrogens relative to the amount of the pharmaceutical support material lying in the range from 43 to 90 mg of conjugated estrogens per gram of support material.

4. A preformulation according to claim 1, wherein said preformulation has a residual moisture content of at most 3.0% by weight, relative to the entire preformulation as 100% by weight.

5. A preformulation according to claim 4, wherein said preformulation has a residual moisture content of at most 1.0% by weight, relative to the entire preformulation as 100% by weight.

6. A preformulation according to claim 1, wherein the active-substance content, calculated as total hormone content, lies in the range from about 35 to 100 mg per gram of the pharmaceutical support material.

7. A preformulation according to claim 6, wherein the active-substance content, calculated as total hormone content, lies in the range from about 43 to 90 mg per gram of the pharmaceutical support material.

8. A preformulation according to claim 1, wherein the proportion of free hormones relative to the total hormone content in the active substance is less than 2% by weight.

9. A preformulation according to claim 1, wherein the pharmaceutical support material is a microcrystalline cellulose or a mixture of microcrystalline celluloses.

10. A preformulation according to claim 1, wherein the pharmaceutical support material is a mixture of microcrystalline cellulose and lactose.

11. A preformulation according to claim 10, wherein the weight ratio of microcrystalline cellulose to lactose lies in the range of 8:2 to 6:4.

12. A preformulation according to claim 11, wherein the weight ratio of microcrystalline cellulose to lactose lies in the range of about 7.5:2.5 to 6.5:3.5.

13. A preformulation according to claim 12, wherein the weight ratio of microcrystalline cellulose to lactose is about 7:3.

14. A preformulation according to claim 1, wherein the mean bulk volume of the preformulation lies in the range from 1.8 to 3.0 ml/g.

15. A preformulation according to claim 1, wherein the mean bulk density of the preformulation lies in the range from 0.3 to 0.6 grams/ml.

16. A preformulation according to claim 1, wherein the preformulation has a particle-size distribution corresponding to the following sieve analysis:

about 0.15% to at most 2% by weight of the particles larger than a mesh size of 250 μm;
about 3 to 31% by weight of the particles larger than a mesh size of 160 μm;
about 8 to 36% by weight of the particles larger than a mesh size of 125 μm; and
fines of the particles of about 3 to at most 23% by weight passing through a sieve mesh size of 63 μm.

17. A preformulation according to claim 1, wherein the preformulation has a mean particle size lying in the range from 50 to 250 μm.

18. A preformulation according to claim 17, wherein the preformulation has a mean particle size lying in the range from 75 to 150 μm.

* * * * *